US012171722B2

(12) United States Patent
McMichael et al.

(10) Patent No.: US 12,171,722 B2
(45) Date of Patent: Dec. 24, 2024

(54) SYSTEM AND METHOD FOR ACOUSTIC SENSING TO VERIFY PROPER NASOGASTRIC TUBE PLACEMENT

(71) Applicant: Avent, Inc., Alpharetta, GA (US)

(72) Inventors: Donald McMichael, Roswell, GA (US); James F. Tassitano, Marietta, GA (US)

(73) Assignee: Avent, Inc., Alpharetta, GA (US)

( * ) Notice: Subject to any disclaimer, the term of this patent is extended or adjusted under 35 U.S.C. 154(b) by 1010 days.

(21) Appl. No.: 16/526,077

(22) Filed: Jul. 30, 2019

(65) Prior Publication Data

US 2021/0030629 A1 Feb. 4, 2021

(51) Int. Cl.
*A61J 15/00* (2006.01)
*A61M 25/01* (2006.01)
*A61M 39/10* (2006.01)

(52) U.S. Cl.
CPC ...... *A61J 15/0088* (2015.05); *A61M 25/0105* (2013.01); *A61M 39/105* (2013.01); *A61J 2200/70* (2013.01); *A61J 2205/20* (2013.01); *A61J 2205/50* (2013.01); *A61M 2025/0166* (2013.01); *A61M 2205/0238* (2013.01); *A61M 2205/0244* (2013.01); *A61M 2205/18* (2013.01); *A61M 2205/3375* (2013.01); *A61M 2205/3523* (2013.01); *A61M 2205/50* (2013.01); *A61M 2205/502* (2013.01); *A61M 2205/52* (2013.01); *A61M 2205/584* (2013.01); *A61M 2205/6018* (2013.01)

(58) Field of Classification Search
CPC ................ A61J 15/0088; A61J 2200/70; A61J 2205/20; A61J 2205/50; A61M 25/0105; A61M 39/105

USPC .......................................................... 600/586
See application file for complete search history.

(56) References Cited

U.S. PATENT DOCUMENTS

| 4,836,214 | A  | 6/1989  | Sramek |
| 4,920,481 | A  | 5/1990  | Danis et al. |
| 6,334,064 | B1 | 12/2001 | Fiddian-Green |
| 6,357,447 | B1 | 3/2002  | Swanson et al. |
| 7,818,155 | B2 | 10/2010 | Stuebe et al. |

(Continued)

FOREIGN PATENT DOCUMENTS

WO    WO 92/17150    10/1992

*Primary Examiner* — Phillip A Gray
(74) *Attorney, Agent, or Firm* — Meunier Carlin & Curfman LLC

(57) ABSTRACT

A tubing assembly for use with electronic catheter guidance systems is provided and includes a catheter and an acoustic sensor. The catheter extends in a longitudinal direction and has a proximal end and a distal end that define a lumen therebetween. Further, the catheter is configured for placement within a patient's digestive tract. The acoustic sensor can be located within the lumen of the catheter or in a sampling chamber connected to the catheter. The acoustic sensor can communicate with a processor to deliver sound data to a display device. The appearance of random spikes on a frequency versus time spectrogram can indicate placement of the catheter in the digestive tract, while a rhythmic/repetitive pattern on a frequency versus time spectrogram can indicate placement of the catheter in the respiratory tract. A catheter guidance system and method for accurately placing a catheter in the digestive tract are also provided.

9 Claims, 11 Drawing Sheets

(56) References Cited

U.S. PATENT DOCUMENTS

| | | |
|---|---|---|
| 8,147,486 B2 | 4/2012 | Honour et al. |
| 8,613,702 B2 | 12/2013 | Feer et al. |
| 8,986,230 B2 | 3/2015 | Nishtala |
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,610,227 B2 | 4/2017 | Elia |
| 9,642,779 B2 | 5/2017 | Elia et al. |
| 9,713,579 B2 | 7/2017 | Elia et al. |
| 2008/0097179 A1 | 4/2008 | Russo |
| 2008/0167607 A1 | 7/2008 | Pfeiffer et al. |
| 2008/0249467 A1 | 10/2008 | Burnett et al. |
| 2012/0016256 A1 | 1/2012 | Mabary et al. |
| 2012/0277619 A1 | 11/2012 | Starkebaum et al. |
| 2013/0225946 A1 | 8/2013 | Feer et al. |
| 2016/0113843 A1 | 4/2016 | Elia et al. |
| 2016/0129223 A1 | 5/2016 | Kirschenman |
| 2016/0331298 A1 | 11/2016 | Burnett et al. |
| 2017/0071502 A1 | 3/2017 | Bennett-Guerrero |
| 2017/0202750 A1 | 7/2017 | Elia |
| 2018/0078195 A1* | 3/2018 | Sutaria .................. A61B 5/068 |
| 2018/0117285 A1* | 5/2018 | Shaughnessy .... A61M 25/0127 |
| 2018/0161249 A1 | 6/2018 | Elia et al. |
| 2018/0289536 A1 | 10/2018 | Burnett |

\* cited by examiner

SYSTEM AND METHOD FOR ACOUSTIC SENSING TO VERIFY PROPER NASOGASTRIC TUBE PLACEMENT

BACKGROUND OF THE INVENTION

Physicians and other health care providers frequently use catheters to treat patients. Known catheters include a tube which is inserted into the human body. Certain catheters are inserted through the patient's nose or mouth for treating the digestive or gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient.

When using these known catheters, it is important to place the end of the catheter at the proper location within the human body. Erroneous placement of the catheter tip may injure or harm the patient. For example, if the health care provider erroneously places an enteral catheter into the patient's trachea, lungs, or other anatomical regions of the respiratory system or airway rather than through the esophagus and to the stomach to reach the desired location in the digestive tract for delivering nutrients or medicine, liquid may be introduced into the lungs with harmful, and even fatal, consequences. In particular, the esophagus of the digestive tract and the trachea of the respiratory system are in close proximity to each other and are blind to the health care provider during catheter placement, which creates a dangerous risk for erroneous catheter placement.

In some cases, health care providers use X-ray machines to gather information about the location of the catheters within the body. There are several disadvantages with using X-ray machines. For example, X-ray machines are relatively large and heavy, consume a relatively large amount of energy and may expose the patient to a relatively high degree of radiation. Also, these machines are typically not readily accessible for use because, due to their size, they are usually installed in a special X-ray room. This room can be far away from the patient's room. Therefore, health care providers may find it inconvenient to use these machines for their catheter procedures. In addition, using X-ray technology is expensive and is a time-consuming task that can create unnecessary delays in delivering critical nutrients to the patient.

Accordingly, there is a need to overcome each of these disadvantages.

SUMMARY OF THE INVENTION

Objects and advantages of the invention will be set forth in part in the following description, or may be obvious from the description, or may be learned through practice of the invention.

In one embodiment, a tubing assembly is provided. The tubing assembly includes a catheter having a proximal end and a distal end and extending in a longitudinal direction, where the proximal end and the distal end define a lumen therebetween, and where the catheter is configured for placement within a digestive tract of a patient; and an acoustic sensor.

In another embodiment, the acoustic sensor can be located within the lumen of the catheter.

In still another embodiment, the tubing assembly can include a sampling chamber. Further, the acoustic sensor can be located within the sampling chamber.

In yet another embodiment, the acoustic sensor can be configured to acquire sound data from sound waves traveling through the lumen from an opening in the distal end of the catheter and communicate the sound data to a processor in real-time. In addition, the acoustic sensor can be configured for a wired connection or a wireless connection to the processor.

In an additional embodiment, the sensor can be protected from fluid ingress by a flexible coating.

In one more embodiment, the tubing assembly can include a multi-port connector. Further, the multi-port connector can include a nutrient branch and a medicine branch.

In another embodiment, the acoustic sensor can be contained within a microelectro-mechanical system (MEMS) microphone.

In one more embodiment, a catheter guidance system is provided. The catheter guidance system includes (a) a processor; (b) a power source; (c) a display device; and (d) a tubing assembly. The tubing assembly includes a catheter having a proximal end and a distal end and extending in a longitudinal direction, where the proximal end and the distal end define a lumen therebetween; and an acoustic sensor. Further, the acoustic sensor communicates sound data acquired by the acoustic sensor from sound waves traveling through the lumen from an opening in the distal end of the catheter to the processor in real-time via an electrical connection, where the display device is coupled to the processor and displays a graph of the sound data communicated by the acoustic sensor; and where the catheter guidance system alerts a user as to correct placement of the catheter in a digestive tract of a patient or alerts the user as to incorrect placement of the catheter in a respiratory tract of the patient.

In another embodiment, the catheter guidance system can further include a memory device storing instructions which, when executed by the processor, cause the processor to (i) interpret the sound data communicated by the acoustic sensor and (ii) cause the catheter guidance system to alert the user as to correct placement of the catheter in the digestive tract of the patient or alert the user as to incorrect placement of the catheter in the respiratory tract of the patient based on the interpretation of the sound data.

In still another embodiment, the acoustic sensor can be located within the lumen of the catheter or within a sampling chamber.

In yet another embodiment, the acoustic sensor can be protected from fluid ingress by a flexible coating.

In an additional embodiment, the acoustic sensor can be contained within a microelectro-mechanical system (MEMS) microphone.

In one more embodiment, a method for determining if a catheter is placed within a digestive tract of a body of a patient is provided. The method includes (a) inserting a distal end of a tubing assembly into an orifice of the body, wherein the tubing assembly comprises: the catheter, wherein the catheter has a proximal end and a distal end and extends in a longitudinal direction, wherein the proximal end and the distal end define a lumen therebetween; and an acoustic sensor; (b) electrically connecting the acoustic sensor to a processor via a wired connection or a wireless connection; (c) activating the acoustic sensor, wherein the acoustic sensor acquires sound data from sound waves traveling through the lumen from an opening in the distal end of the catheter and communicates the sound data to the processor in real-time via the wired connection or the wireless connection; (d) advancing the distal end of the catheter inside the body in a direction away from the orifice while the acoustic sensor is activated; and (e) observing a graph of the sound data on a display device coupled to the processor, wherein the display device alerts a user as to correct placement of the catheter in the digestive tract of the patient or alerts the user as to incorrect placement of the catheter in a respiratory tract of the patient.

In another embodiment, a memory device can store instructions which, when executed by the processor, cause the processor to (i) interpret the sound data communicated by the acoustic sensor and (ii) cause the display device to communicate whether or not the catheter is placed within the digestive tract of the patient based on the interpretation of the sound data.

In still another embodiment, the orifice can be a nose or a mouth.

In yet another embodiment, the acoustic sensor can be located within the lumen of the catheter or within a sampling chamber.

In an additional embodiment, the acoustic sensor can be contained within a microelectro-mechanical system (MEMS) microphone, and the acoustic sensor can be protected from fluid ingress by a flexible coating.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
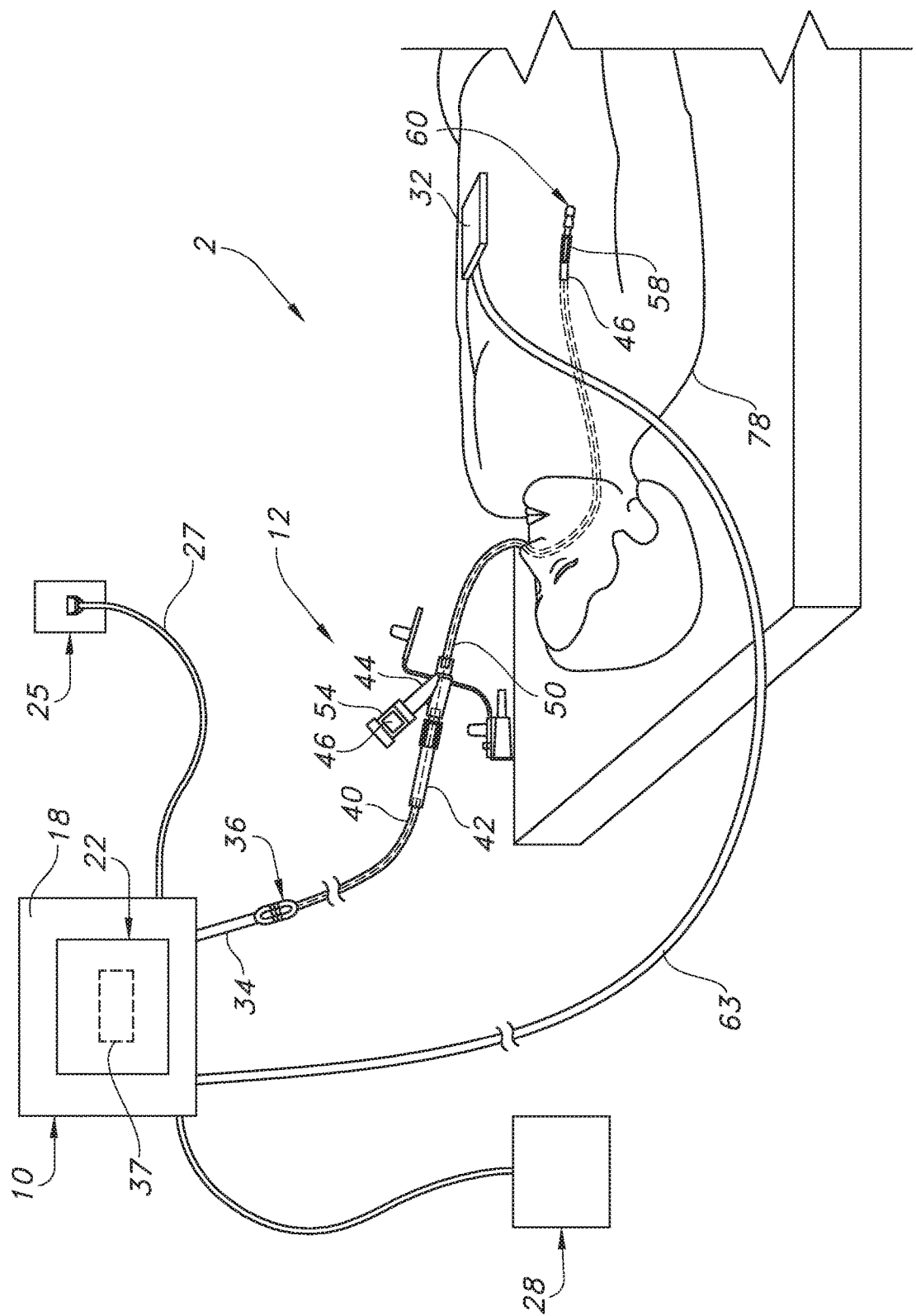
FIG. 1 is a perspective view of the catheter guidance system of the present invention illustrating the display device, electronic catheter unit and the acoustic sensor that is at least temporarily contained with the electronic catheter unit as it is being used to position a catheter within a patient in one embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention is directed to a tubing assembly that includes a catheter having a proximal end and a distal end and extending in a longitudinal direction, where the proximal end and the distal end define a lumen therebetween. Further, the catheter is configured for placement within a digestive tract of a patient. The tubing assembly also includes an acoustic sensor. The acoustic sensor can be located within the lumen of the catheter or in a sampling chamber connected to the catheter. The acoustic sensor can communicate with a processor to deliver sound data to a display device. The appearance of random spikes on a frequency versus time spectrogram graph shown on the display device can indicate placement of the catheter in the digestive tract, where the random spikes are associated with contact noises between the catheter and an anatomical region in the digestive tract (e.g., the epiglottis, esophagus, stomach, intestine, etc.). Meanwhile, the appearance of a rhythmical pattern (e.g., a sinusoidal wave) on a frequency versus time spectrogram graph shown on the display device can indicate erroneous placement of the catheter in the respiratory system (e.g., the trachea, bronchi, lungs, etc.). A catheter guidance system and a method for accurately placing a catheter in the digestive tract are also contemplated by the present invention.

The present inventors have found that the tubing assembly, catheter guidance system, and method described in more detail herein allow for the sound data captured in real-time via the acoustic sensor to be used to determine if the distal end of the catheter is accurately placed within the digestive tract (e.g., the epiglottis, esophagus, stomach, intestines, etc.) rather than erroneously placed within the respiratory system (e.g., the trachea, bronchi, lungs, etc.), where such placement could be harmful and even fatal to a patient. Further, the present inventors have found that because the acoustic sensor can obtain measurements and communicate those measurements to processor and ultimately a display device or other communication device (e.g., a phone, pager, etc.) in real time, the correct placement of the catheter can be confirmed within seconds of a catheter placement procedure, which can save valuable time, resources, and cost while at the same time limit patient risk in the event of the erroneous placement of the catheter.

Specifically, the present inventors have found that capturing and monitoring sound data in real-time of air inside or within a catheter to be placed in a predetermined location along the digestive tract (e.g., esophagus, stomach, intestines, etc.), which is facilitated by the acoustic sensor of the catheter guidance system of the present invention, allows for the efficient and accurate placement of the catheter within the digestive tract at a low cost. For instance, the acoustic sensor in the tubing assembly can capture sound data (e.g., sound waves, vibratory responses, etc. that propagate from a distal end of the catheter to the acoustic sensor) within the catheter as it is being directed by a health care provider in to the body of a patient, where the captured sound data can then be transmitted to a display device via a processor. The health care provider can then view the captured sound data on the display device (e.g., on a spectrogram that plots the captured sound data of a graph showing frequency versus time) to determine if the catheter has been accurately placed in the digestive tract or erroneously placed in an anatomical region of the respiratory system (e.g., the trachea, bronchi, lungs, etc.). Alternatively or additionally, a memory device that can include machine readable instructions and one or more computer programs (which, for example, may include a plurality of algorithms) can be used by the processor to process the data from the acoustic sensor, where the display device can then indicate the catheter information to the health care provider in the form of a signal as to whether the catheter is accurately placed in the digestive tract or erroneously placed within, for instance, a portion of the respiratory system. For example, a green check mark or the word "Yes" can be displayed on the screen to indicate accurate placement of the catheter within the digestive or gastrointestinal tract, while a red circle with a diagonal line through it, an "X", or the word "No" can be displayed on the screen for erroneous placement, such as placement within the respiratory system.

The various features of the catheter guidance system are discussed in detail below.

Referring now to the drawings, in an embodiment illustrated in FIGS. 1-4, the catheter guidance system 2 contemplated by the present invention includes: (a) an apparatus 10 having a housing 18 which supports a controller or processor 20 and a display device 22; (b) a power cord 27 that couples the apparatus 10 to a power source 25; (c) a printer 28 coupled to the apparatus 10 for printing out paper having graphics which indicate catheter location information; (d) an optional non-invasive movable receiver-transmitter or transceiver 32 electronically coupled to the processor 20 by a wire, cable, signal data connection or signal carrier 63; and (e) an invasive electronic catheter unit 12 in communication with and operatively coupled to the apparatus 10 by a wire, cable, cord or electrical extension 34, which, in turn, is operatively coupled to the processor 20, where the electronic catheter unit 12 includes a tubing assembly 14 that includes a catheter 50; an acoustic sensor 46; and an optional signal generator 58 when the system 2 includes the optional non-invasive movable receiver-transmitter or transceiver 32.

Figure 2:
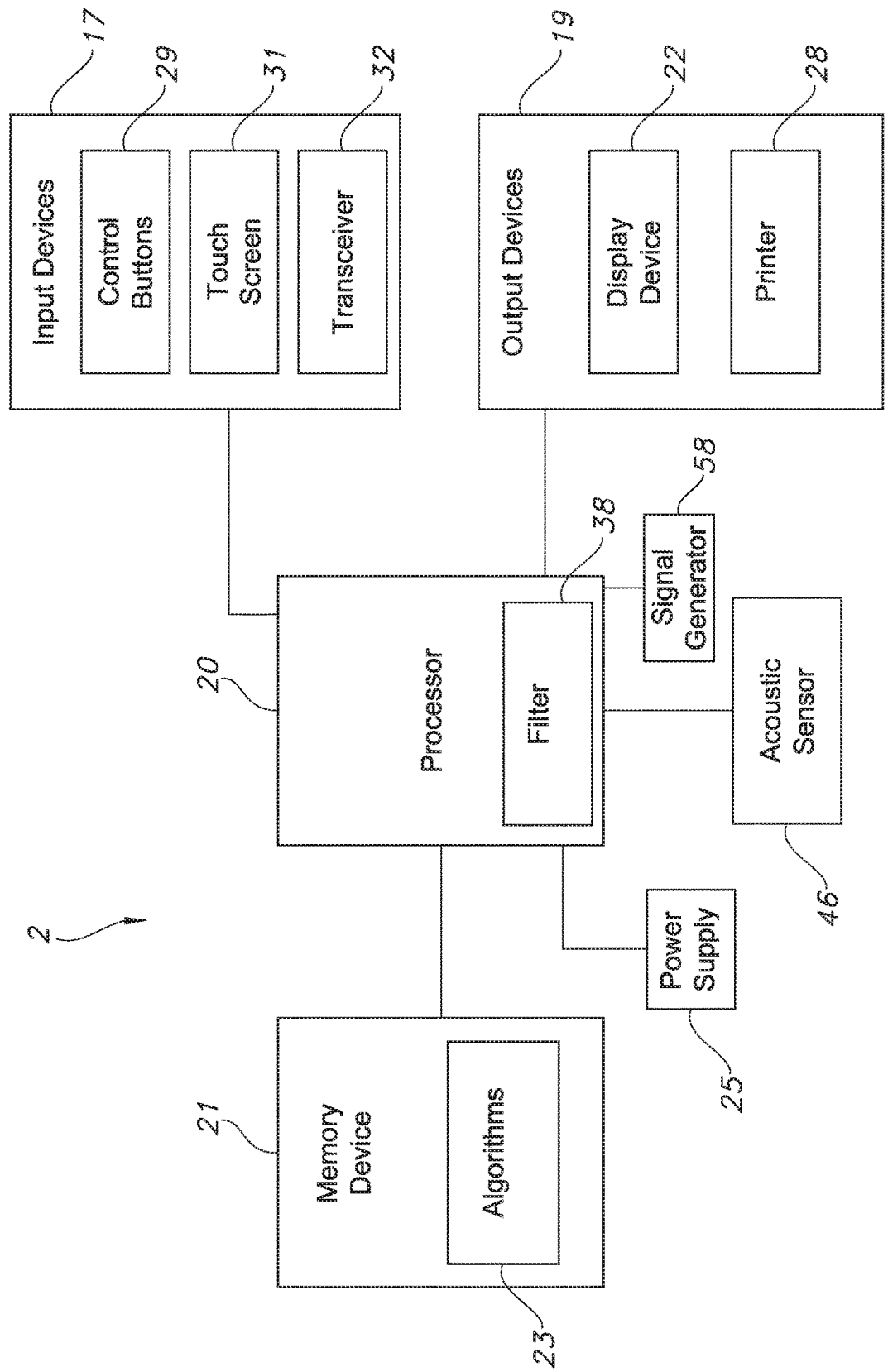
FIG. 2 is a schematic block diagram of the electronic configuration of the catheter position guidance system illustrating the processor, memory device, acoustic sensor, input devices, output devices, and optional signal generating assembly according to one embodiment of the present invention.
Figure 3:
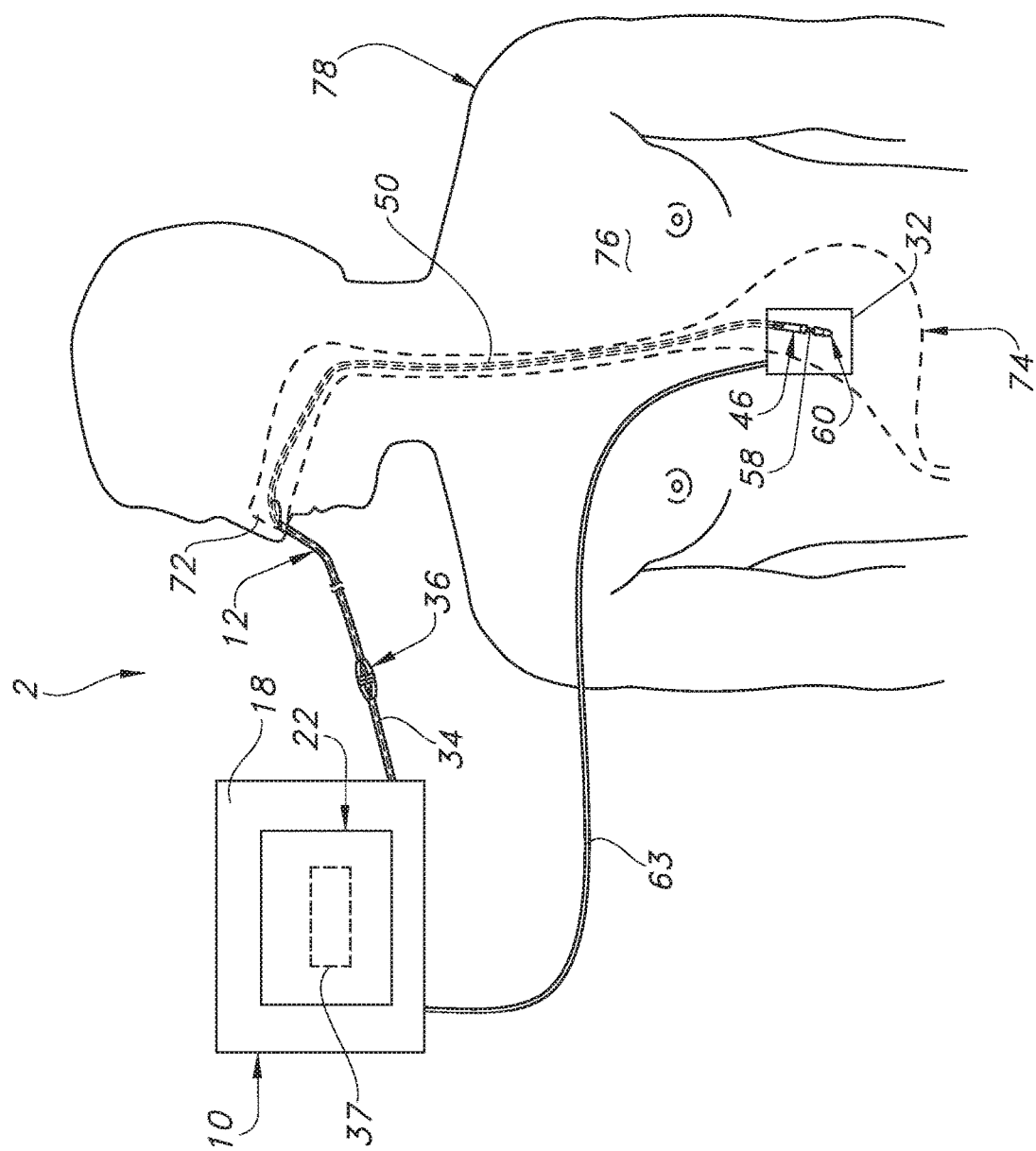
FIG. 3 is a top or plan view of the electronic catheter unit and the display device illustrating an enteral application involving a catheter inserted into a human body and indication of acoustic sensor information (e.g., a graph) on the display device.

As best illustrated in FIG. 2, the system 2, in one embodiment, includes: (a) a plurality of input devices 17 for providing input signals to the system 2 such as one or more control buttons 29, a touch screen 31, and the optional transceiver 32; (b) an acoustic sensor 46 that can continuously capture sound data from a vibratory response and/or sound waves traveling inside or within a catheter 50 of the tubing assembly 14 in real-time; (c) an optional signal generator 58 which produces or generates electronic signals that are received by the transceiver 32; (d) a memory device 21 including machine readable instructions and one or more computer programs (which, for example, may include a plurality of algorithms 23) which are used by the processor 20 to process the sound data captured by the acoustic sensor 46 as well as to process the signal data produced by the signal generator 58 and transmitted by the transceiver 32 if present; and (e) a plurality of output devices 19 such as the display device 22 and the printer 28 which indicate the catheter information to the health care provider, such as in the form of a graph 37 (see FIGS. 1, 6B, 7B, and 8B). The display device 22 may be any suitable display mechanism including, but not limited to, a liquid crystal display (LCD), light-emitting diode (LED) display, cathode-ray tube display (CRT) or plasma screen.

In one particular embodiment, the memory device 21 can store instructions which, when executed by the processor 20, cause the processor 20 to (i) interpret catheter 50 location and/or position information as determined and communicated by the acoustic sensor 46 and the optional signal generating assembly 16 and the non-invasive transceiver 32, and (ii) cause the processor 20 to then instruct the system 2 to alert the health care provider either via the display device 22, auditory signals, etc. as to the accurate or inaccurate placement of the catheter 50.

Figure 4:
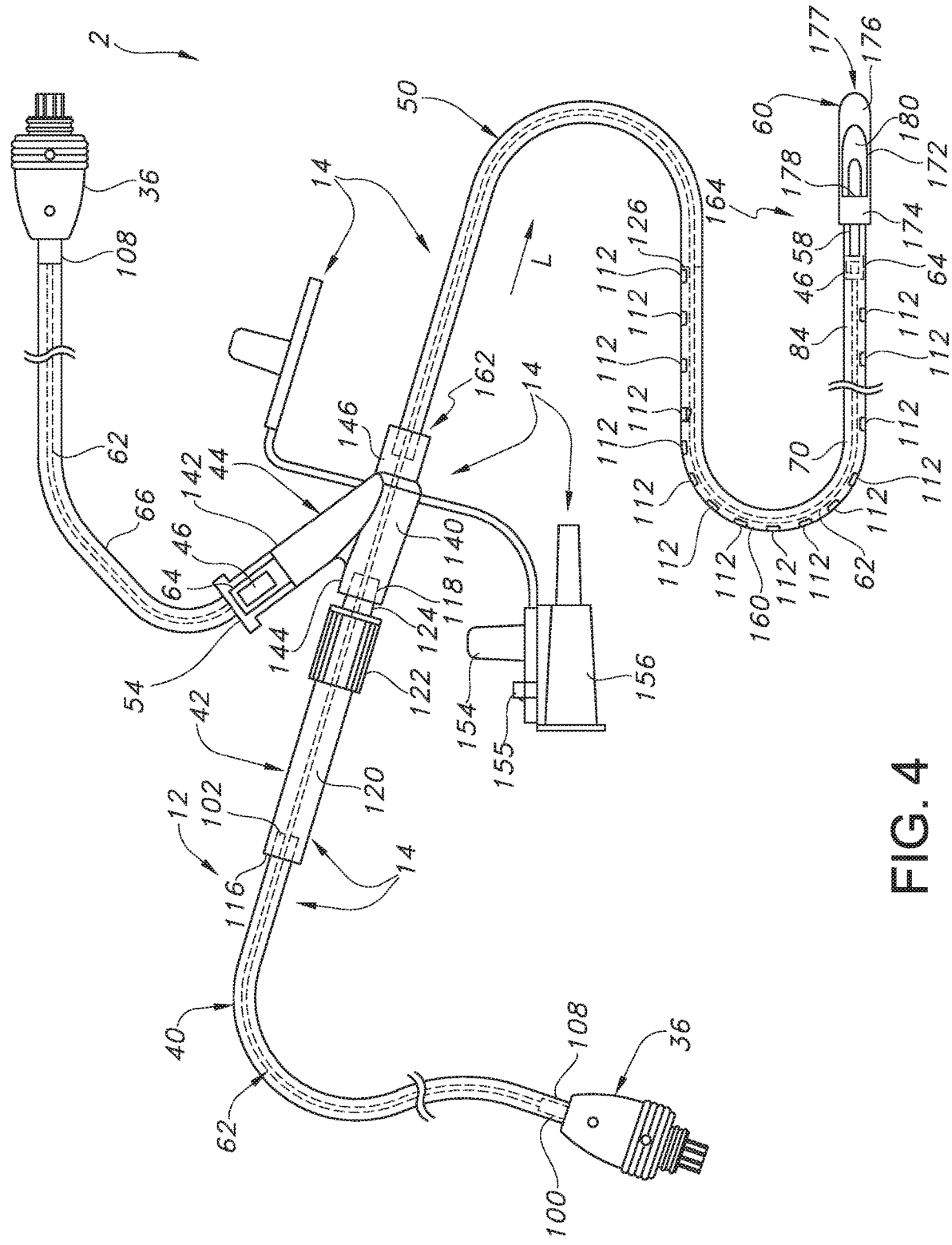
FIG. 4 is a perspective view of the electronic catheter unit illustrating the tubing assembly and the various locations for the acoustic sensor according to various embodiments of the present invention.

Health care providers can use the system 2 in a variety of catheter applications. In one example illustrated in FIG. 3, the system 2 is used in an enteral application. Here, a portion of the electronic catheter unit 12 is placed through an orifice 72 of the patient, such as the patient's nose or mouth. The distal end or tip 60 of the electronic catheter unit 12 can ultimately by positioned in the stomach 74. As the health care provider advances the catheter 50 of the electronic catheter unit 12 towards the patient's stomach 74, the acoustic sensor 46 can continuously monitor for sound waves or vibratory responses that propagate from the distal end 60 of the catheter 50 to the acoustic sensor 46 as the catheter 50 is inserted by the health care provider, whether the acoustic sensor 46 is placed at the distal end or tip 60 of the catheter 50 or more upstream, such as in a sampling chamber 54 as shown in FIGS. 1 and 4. The display device 22 and the printer 28 can indicate information related to the location of the portion of the electronic catheter unit 12 within the body 78 based on the sound data acquired by the acoustic sensor 46, as well as information related to the shape of the pathway taken by the catheter unit 12 if the system includes the signal generator 58 and the associated non-invasive transceiver 32. It should be appreciated that the system 2 need not indicate the exact location or path of the catheter unit 12 to provide assistance to the health care provider.

Referring to FIG. 4, in one embodiment, the electronic catheter unit 12 includes a tubing assembly 14, which includes the catheter 50 and the acoustic sensor 46 of the present invention, where the catheter 50 can generally extend in the longitudinal direction L. In one embodiment, the acoustic sensor 46 can be disposed within the lumen 70 of the catheter 50 at a distal end or tip 60 of the catheter 50, as shown in FIG. 4. However, it is also to be understood that the acoustic sensor 46 can be located anywhere along the length of the catheter 50, so long as the sound waves entering the catheter 50 from opening 180 at the distal end 60 of the catheter can reach or be picked up by the acoustic sensor 46. In another embodiment, for instance, the electronic catheter unit 12 can include a sampling chamber 54 that can alternatively house the acoustic sensor 46 upstream from the distal end 60 of the catheter 50.

Figure 5:
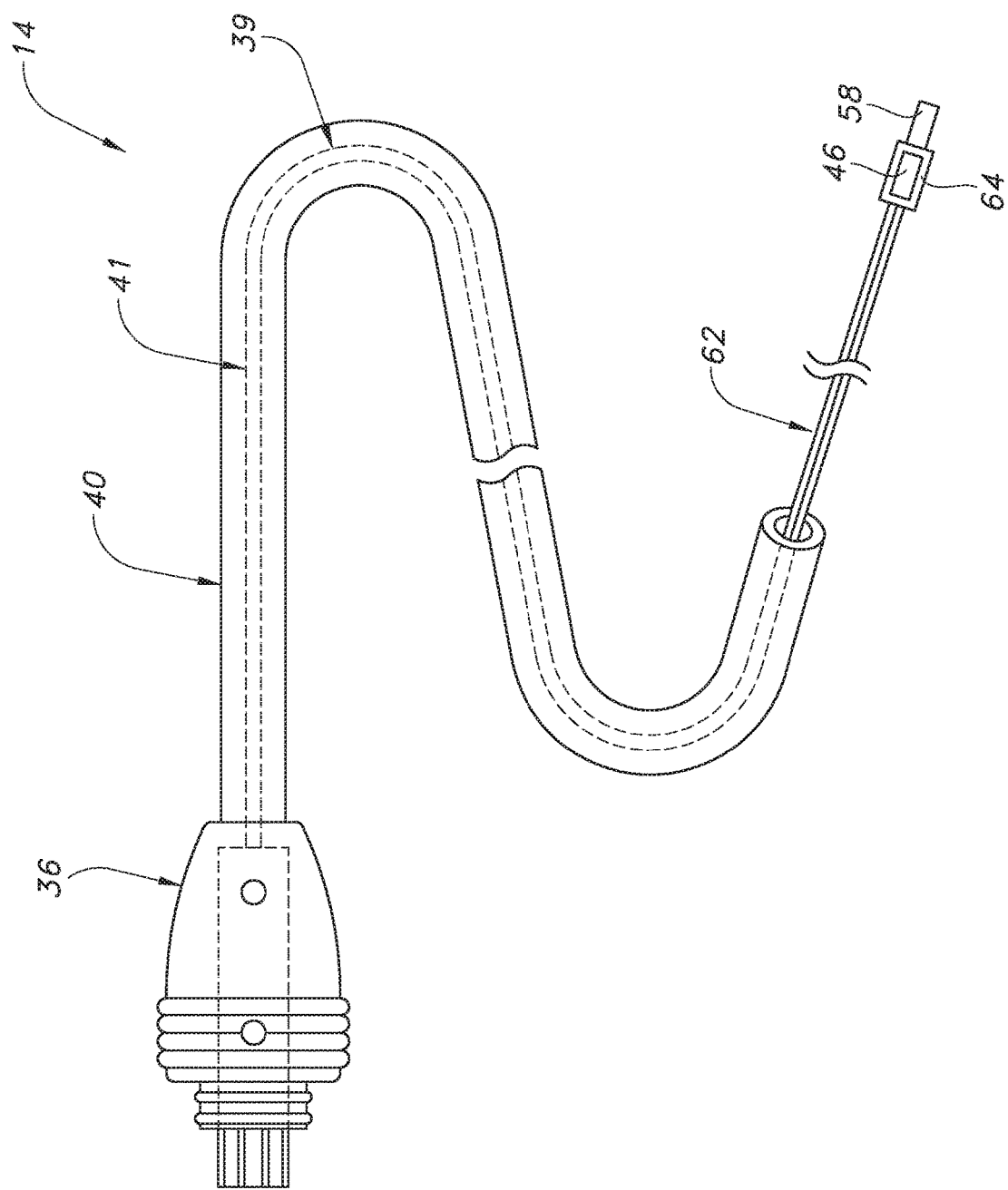
FIG. 5 is a perspective view of the acoustic sensor portion of the electronic catheter unit according to one embodiment of the present invention.

As best illustrated in FIGS. 4-5, in one embodiment, such as when a wired connection (e.g., a connection via a wire assembly 62 as opposed to a wireless connection, which is also contemplated by the present invention, where the acoustic sensor 46 includes a battery or other source of power) electrically connects the acoustic sensor 46 to the processor 20, the tubing assembly 14 can include (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) a distal end or tip 60 of the catheter 50, where the acoustic sensor 46 can be located within the lumen 70 of the catheter 50 at the distal end or tip 60 or anywhere upstream along the length of the catheter 50.

In one embodiment, the tubular insulator 40 includes a tube having a proximal end 100 attachable to an attachment member or neck 108 of a controller coupler or electrical connector 36 and a distal end 102 receivable by the union device 42; and an internal diameter which is substantially equal to or greater than an external diameter of a wire assembly 62 described below, which can serve as the hard wired electrical connection between the acoustic sensor 46 and the processor 20, so as to slide over the wire assembly 62. In another embodiment, the tubular insulator 40 may fit relatively tightly over the wire assembly 62 so as to be secured to the wire assembly 62.

As best illustrated in FIG. 4, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; and (e) an insert 124 positioned adjacent to the gripping member 122 which is received by the y-port connector 44. When assembled, the proximal end 116 of the union device 42 is coupled to the distal end 102 of the tubular insulator 40.

In one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or movable arm 150 attached to the body 140. In an alternative embodiment, y-port connector 44 includes additional branches for administering various nutrients or medicines to the body 78.

In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

As illustrated in FIG. 4, in one embodiment, the catheter 50 includes a feeding tube or catheter 50 with a body 160 having a proximal end 162 attached to the catheter connection branch 146 of the y-port connector 44 and a distal end 164. The proximal end 162 is insertable into the catheter connection branch 146 of the y-port connector 44 so as to bring the catheter 50 into fluid communication with the y-port connector 44.

As also shown in FIG. 4, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged.

The tubular connector 40, union device 42, y-port connector 44, catheter 50, and tip 60 can be made from any suitable polymer or plastic material including, but not limited to, polyamide, polyethylene, polypropylene, polyurethane, silicone and polyacrylonitrile.

Referring still to FIGS. 1 and 4, in some embodiments, the tubing assembly 14 can include a sampling chamber 54 that can house the acoustic sensor 46 when the acoustic sensor 46 is not integrated into the distal end 60 of the catheter. In such an embodiment, the acoustic sensor 46 can be wireless or, alternatively, the acoustic sensor 46 can be electrically connected to the processor 20 via the wire assembly 62 that extends through the sampling chamber 54 and through tubing 66 to an electrical connector or controller coupler 36. As shown in FIGS. 1 and 4, the sampling chamber 54 can be coupled to the delivery branch or medicine branch 142 of the multi-port connector or y-port connector 44. Meanwhile, when the acoustic sensor 46 is located in the lumen 70 of the catheter 50 such as its distal end 60, the acoustic sensor 46 can be electrically connected to the processor 20 via an electrical connection in the form of a wire assembly 62 that runs through the tubular insulator 40 described above to an electrical connector or controller coupler 36, discussed in more detail below. This arrangement can also be used when the electrical connection from the sensor 46 to the processor 20 is wireless.

Turning now to the specifics of the acoustic sensor 46 and referring to FIGS. 1, 4, and 5, a controller coupler or an electrical connector 36 can be operatively connected to the electrical extension 34 and an elongated wire assembly 62 can be operatively coupled to the electrical connector 36 to form a wired connection between the acoustic sensor 46 and the processor 20, although it is to be understood that the electrical connection between the processor 20 and the acoustic sensor 46 can also be wireless provided that the acoustic sensor 46 has its own power source, such as a battery. Further, a wire or elongated stiffener 39 can be attached to the connector 36 and can serve as a support for the wire assembly 62 when it is inserted into the body 160 of the catheter 50 or the tubing 66. Further, the tubular insulator 40 described above can cover a portion 41 of the wire assembly 62 positioned adjacent to the connector 36 in the embodiment where the acoustic sensor 46 is positioned within the lumen 70 of the catheter 50. In any event, the electrical connector or controller coupler 36 can provide the electrical connection between the apparatus 10 and the acoustic sensor 46 when the acoustic sensor 46 is hard wired to the catheter guidance system 2 via the wire assembly 62, regardless of whether the acoustic sensor 46 is positioned within the lumen 70 of the catheter or within the sampling chamber 54.

Turning now to the specific configuration for the acoustic sensor 46, although any suitable acoustic sensor 46 for acquiring data from sound saves that propagate from the opening 180 in the distal end 60 of the catheter 50 that can withstand the environmental conditions of the body can be used in the catheter guidance system 2 of the present invention, in one particular embodiment, the acoustic sensor 46 can be in the form of a MEMS (microelectro-mechanical system) microphone having a small footprint such that it can be placed within the lumen 70 of the catheter 50, the sampling chamber 54, or any other suitable location within the tubing assembly 14. Specifically, benefits of the use of a MEMS microphone include a high signal to noise (SNR) ratio, low power consumption, good sensitivity, and a small size. Further, MEMS microphones exhibit almost no change in performance after reflow soldering and have excellent temperature characteristics. In general, MEMS microphones use acoustic sensors that are fabricated on semiconductor production lines using silicon wafers and highly automated processes. Layers of different materials can be deposited on top of a silicon wafer, after which any unwanted material is then etched away, creating a moveable membrane and a fixed backplate over a cavity in the base wafer. The sensor backplate is a stiff perforated structure that allows air to move easily through it, while the membrane is a thin solid structure that flexes in response to the change in air pressure caused by sound waves. Changes in air pressure created by sound waves cause the thin membrane to flex while the thicker backplate remains stationary as the air moves through its perforations. The movement of the membrane creates a change in the amount of capacitance between the membrane and the backplate, which is translated into an electrical signal by an application-specific integrated circuit (ASIC) located inside the MEMS microphone.

The ASIC inside a MEMS microphone typically uses a charge pump to place a fixed charge on the microphone membrane. The ASIC then measures the voltage variations caused when the capacitance between the membrane and the fixed backplate changes due to the motion of the membrane in response to sound waves propagated from the distal end 60 of the catheter 50 as it is inserted to the desired location in the body 78. When the MEMS microphone is an analog microphone, the microphone produces an output voltage that is proportional to the instantaneous air pressure level. The design of an analog MEMS microphone requires careful design of the PCB and cables to avoid picking up noise between the microphone output and the input of the integrated circuit receiving the signal, and a low noise audio analog to digital converter may be needed to convert the output of analog MEMs microphone into a digital format for transmission and processing via the processor 20.

Meanwhile, digital MEMS microphones have digital outputs that switch between low and high logic levels. Most digital microphones use pulse density modulation (PDM), which produces a highly oversampled single-bit data stream. The density of the pulses on the output of a microphone using pulse density modulation is proportional to the instantaneous air pressure level. Digital MEMS microphone outputs are relatively immune to noise, but signal integrity can still be a concern due to distortion created by parasitic capacitance, resistance, and inductance between the microphone output and the system on chip (SoC).

Thus, whether the acoustic sensor 46 is in the form of an analog MEMS microphone or a digital MEMS microphone, the sound data or signals transmitted from the acoustic sensor 46 to the processor 20 may first pass through a filter assembly 38 to remove unwanted noise from the captured sound data and amplify the frequencies of interest before being processed and presented to the display device 22 via the processor 20 and its associated algorithms 23 stored in the memory device 21, although when the acoustic sensor 46 is a digital sensor, a filter 38 may not be needed and the sound data or signals can be transmitted directly to the processor 20. The filter 38 can be in the form of a hardware filter, a software filter, or a combination thereof. Further, the filter 38 can include a combination of a low pass filter and a high pass filter. When the acoustic sensor 46 is an analog sensor, the filter 38 can include a hardware low pass filter and a hardware high pass filter. In addition, once the sound data or signals are filtered, an analog to digital converter can convert the sound data or signals to digital format, where the signal can then be sent to the processor 20 for further analysis. Meanwhile, when the acoustic sensor 46 is a digital sensor, the filter 38 can be a digital software filter that can be implemented to remove both low frequency and high frequency bands.

Regardless of the specific type of filter 38 utilized, the filter 38 can be used to optimize the quality of the sound data or signals from the acoustic sensor 46 in order to accurately determine if a catheter is placed within a digestive tract of a patient or in a respiratory tract of the patient. For instance, the system 2 must be able to accurately identify signals or sound data associated with inspiration and expiration, where the frequency ranges of the breathing sounds associated with inspiration and expiration typically range from about 100 Hertz to about 2,000 Hertz. However, a majority of the power associated with inspiration and expiration breathing sounds falls within the range of about 100 Hertz to about 600 Hertz. On the other hand, sounds associated with the heart and muscle are typically less than about 100 Hertz. Thus, in order to accurately identify inspiration and expiration breathing sounds, filtering out frequencies less than about 100 Hertz, which would filter out those sounds associated with heart and muscle, can enable a more accurate determination of whether or not the tubing assembly of the present invention is being inserted into the respiratory tract or airway. Thus, the low pass filter used in the filter arrangement of the present invention can have a cutoff of about 100 Hertz. On the other hand, the high pass filter used in the filter arrangement of the present invention can have a cutoff of about 1800 Hertz, although it is to be understood that the low frequency and high frequency cutoffs can be adjusted as needed to optimize performance of the catheter guidance system 2 of the present invention. For instance, in some embodiments, the filter 38 can allow sound data or signals associated with frequencies ranging from about 100 Hertz to about 1800 Hertz, such as from about 125 Hertz to about 1400 Hertz, such as from about 150 Hertz to about 1000 Hertz to pass through to the processor 20 for further analysis.

In addition, whether the acoustic sensor 46 is disposed within the lumen 70 of the catheter 50 or within the sampling chamber 54, the acoustic sensor 46 can be surrounded by a coating 64 to prevent moisture from the opening 180 in the tip 60 of the catheter 50 from damaging the electronic components of the acoustic sensor 46 while still allowing the acoustic sensor 46 to detect changes in air pressure created by sound waves propagated from the opening 180 in the distal end 60 of the catheter 50 to the acoustic sensor 46. For instance, the coating 64 can prevent water or other fluid present in the digestive tract or respiratory tract that may enter through the opening 180 from contacting the acoustic sensor 46, while still allowing sound waves to propagate through the lumen 70. In any event, the coating 64 protects the acoustic sensor 46 from water or other fluid ingress that may damage the acoustic sensor 46 or affect the accuracy of the sound data that it acquires. In some embodiments, the coating 64 can be a flexible coating in the form of a thin layer of silicone, polyurethane, or any other material of combination of materials that still allows the acoustic sensor 46 to flex in response to changes in air pressure created by the propagated sound waves.

Figure 6A:
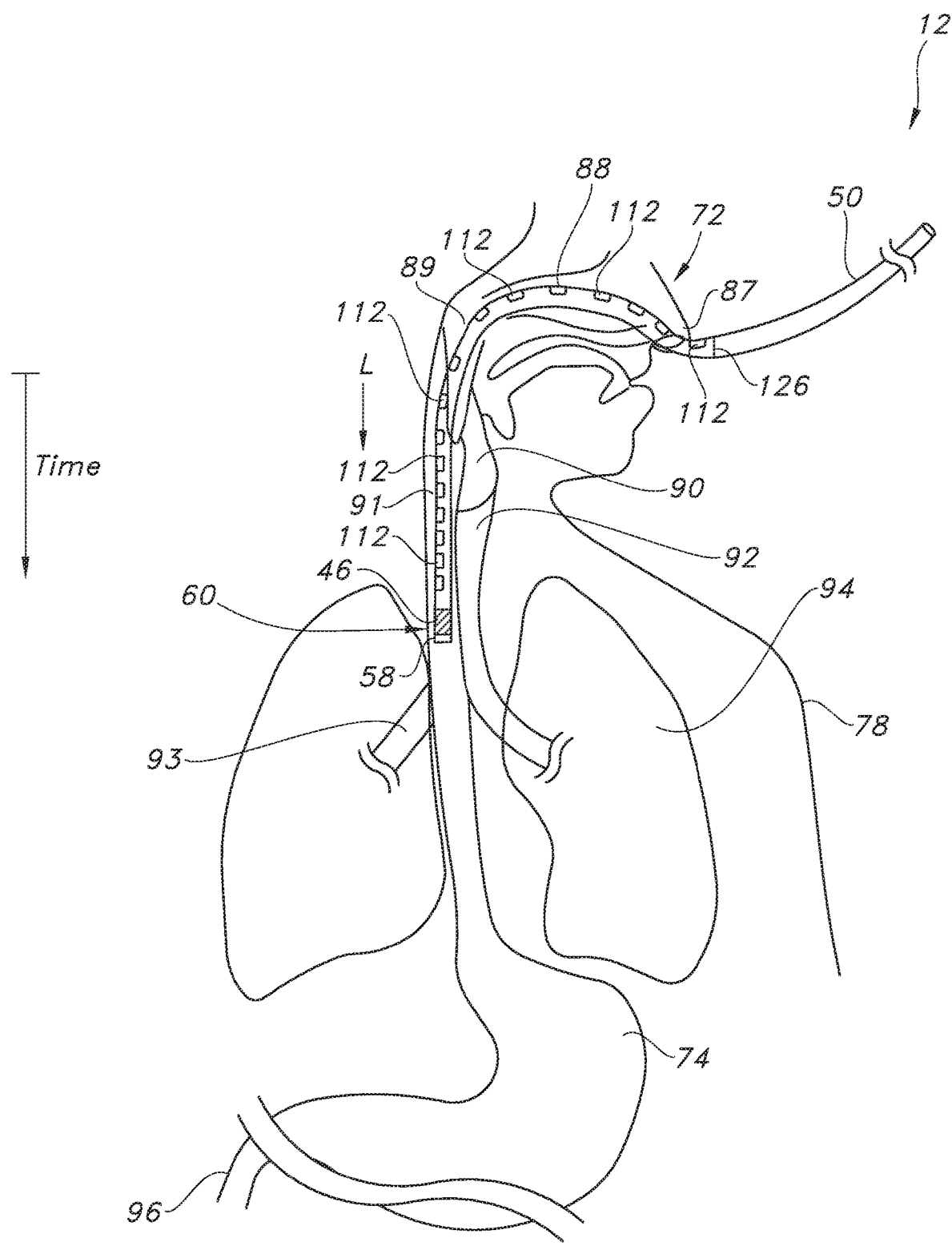
FIG. 6A is a top or plan view of a portion of the electronic catheter unit illustrating an enteral application involving insertion of a catheter into the esophagus of a patient, where the anatomical location of the catheter within the body can be monitored via sound data captured by the acoustic sensor of the present invention.

Further, in one embodiment and referring to FIGS. 4 and 6A, the catheter body 160 can have a plurality of markings 112 uniformly spaced along its external surface that can be used in conjunction with the acoustic sensor 46 to determine accurate placement of the catheter 50. These markings 112 can function as placement markers which assist the user in assessing the depth that the catheter 50 is placed within the body 78. For instance, when the acoustic sensor 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the user can be alerted to start monitoring the graphs 37 on the display device 22 to observe the frequency versus time spectrograms plotted from sound data measured by the acoustic sensor 46 or to start monitoring for a visual indication, auditory indication, or both that the catheter 50 has be inserted into the correct (e.g., digestive tract) or incorrect location (e.g., respiratory tract). For example, if the appearance of a rhythmical pattern (e.g., a sinusoidal wave) on a frequency versus time spectrogram shown on the display device 22 is present once the markings 112 are no longer visible outside the body 78, then the user will be able to determine that the catheter 50 has been improperly inserted into the trachea 92 instead of the esophagus 91, and the catheter 50 should be immediately retracted. In an alternative embodiment, these markings 112 can assist the user in measuring the flow or distribution of liquid to or from the patient.

Now that the specific components of the catheter guidance system 2 have been discussed in detail, a method of using the catheter guidance system 2 of the present invention in order to verify the accurate placement of a catheter 50 used for enteral feeding in the digestive tract is discussed in more detail below with reference to FIGS. 6A-8B.

Generally, the method for determining if the catheter 50 is accurately placed within a digestive tract of a body 78 of a patient includes inserting a distal end of the tubing assembly 14 (e.g., the distal end or tip 60 of the catheter 50) into an orifice 72 of the body 78, such as a nostril 87 of the patient's nose. As described above, the tubing assembly 14 can include the catheter 50 and the acoustic sensor 46. Once the tubing assembly 14 is inserted into the orifice 72 of the body 78, the acoustic sensor 46 can be electrically connected to a processor 20 via a wired connection, such as the wire assembly 62, although a wireless connection is also contemplated by the present invention such that no wire assembly 62 or controller coupler 36 is required).

Next, the acoustic sensor 46 is activated, such as by providing power to the acoustic sensor 46, and the acoustic sensor 46 then begins to measure the changes in air pressure exhibited by air entering the lumen 70 of the catheter 50 from the opening 180 in the distal end 60 and then communicates with the processor 20 via the wired connection (e.g., wire assembly 62) or the wireless connection to deliver the acquired sound data to the processor 20 in real-time.

In addition, a display device 22 is coupled to the processor 20 and displays the sound data communicated to the processor 20 by the acoustic sensor 46 for a health care provider to use during the catheter insertion procedure, where the sound data may first pass through a filter 38 to remove unwanted noise and amplify the frequencies of interest. The filtered data can then be presented as a spectrogram on the display device 22, where differences in random contact noise associated with catheter insertion into the digestive tract and noise associated with respiration with catheter insertion into the respiratory tract can be easily identified by the health care provider via the graphs 37 on the display device 22. Alternatively or additionally, the memory device 21 can store instructions which, when executed by the processor 20, cause the processor 20 to interpret catheter 50 location and/or position information as determined and communicated by the acoustic sensor 46 and the optional signal generating assembly 16 and the non-invasive transceiver 32 and cause the processor 20 to then instruct the system 2 to alert the health care provider either via the display device 22, auditory signals, etc. as to the accurate or inaccurate placement of the catheter 50.

Specifically, the appearance of random spikes on a frequency versus time spectrogram graph 37 shown on the display device 22 can indicate placement of the catheter 50 in the digestive tract, where the random spikes are associated with contact noises between the catheter 50 and an anatomical region in the digestive tract (e.g., the epiglottis 90, esophagus 91, stomach 74, intestine 94, etc. or other anatomical region of the digestive tract of a patient). Meanwhile, the appearance of a rhythmical pattern (e.g., a sinusoidal wave) on a frequency versus time spectrogram graph 37 shown on the display device 22 can indicate erroneous placement of the catheter in the respiratory system (e.g., the trachea 92, bronchi 93, lungs 94, etc. , or other anatomical region of the respiratory tract of the patient) at which time the insertion procedure should be stopped immediately and the tubing assembly 14 be removed from the respiratory tract to avoid potential harm to the patient. Further, in order for such information to be displayed or otherwise communicated by the display device 22, a memory device 21 stores instructions which, when executed by the processor 20, cause the processor 20 to (i) interpret the sound data communicated by the acoustic sensor 46 and (ii) cause the display device 22 to communicate whether or not the catheter 50 is accurately placed within the digestive tract of the patient based on the interpretation of the sound data.

The present inventors have found that the distinctions between auditory or sound profiles of sounds waves propagating from the opening 180 at the distal end 60 of the catheter 50 (either via placement of the acoustic sensor 46 in the lumen 70 of the catheter 50 itself or placement of the acoustic sensor 46 in a sampling chamber upstream) when the distal end or tip 60 of the catheter 50 is placed within the digestive tract or respiratory system are allow for an efficient and possibly life-saving determination of accurate enteral feeding catheter 50 placement in the digestive tract, where erroneously placing the catheter in the respiratory system would deliver fluid into the lungs, which can have fatal consequences.

Figure 6B:
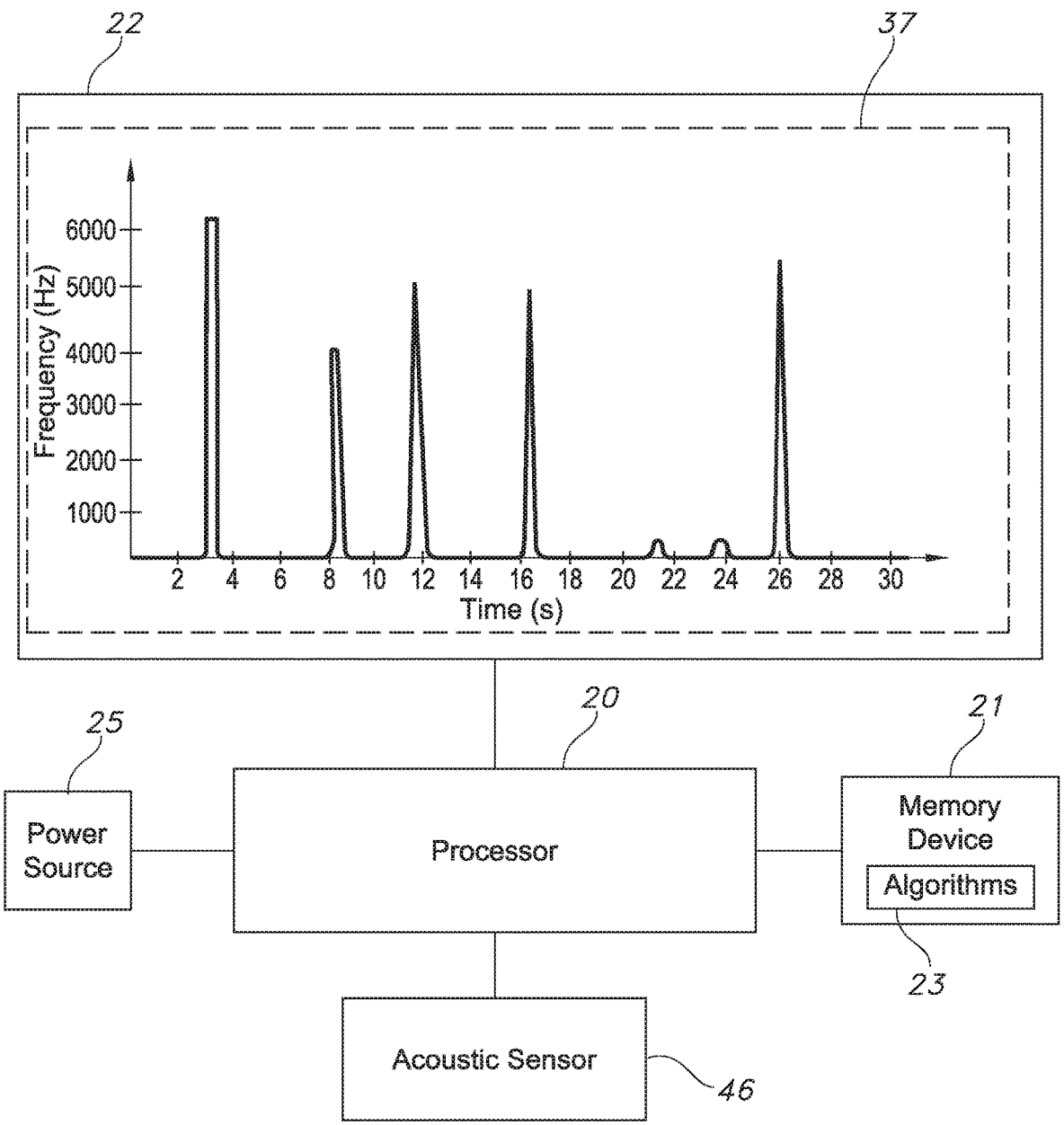
FIG. 6B is a schematic view of the catheter guidance system of the present invention as the system captures sound data associated with contact noises from the catheter of FIG. 6A comes into physical contact with the esophagus and other anatomical regions of the digestive tract in real-time via the acoustic sensor of the present invention.

For instance, as shown in FIGS. 6A and 6B, when the distal end or tip 60 of the catheter 50 is inserted into the nostril 87 of the patient and is advanced through the nasal cavity 88, past the nasopharynx 89, and into the esophagus 91 just past the epiglottis 90, as the acoustic sensor 46 is continuously receiving, recording, and/or processing sound waves propagating through the opening 180 in the distal end 60 of the catheter 50 over time in seconds (whether the acoustic sensor 46 is in the lumen 70 of the catheter 50 itself or in a sampling chamber 54 as shown in FIGS. 1 and 4), the frequency versus time spectrogram graph 37 (FIG. 6B) displayed or otherwise communicated by the processor 20, such as via the display device 22, may show random spikes associated with contact noises as the distal end or tip 60 of the catheter 50 travels into the digestive tract and not into the respiratory system. With insertion of the catheter 50 accurately into the digestive tract, the random spikes associated with contact noise may continue as the distal end or tip 60 reaches the esophagus 91 and is not exposed to the rhythmical pattern of breathing associated with inspiration and expiration, where the frequency versus time spectrogram graph would show a repetitive pattern.

Figure 7A:
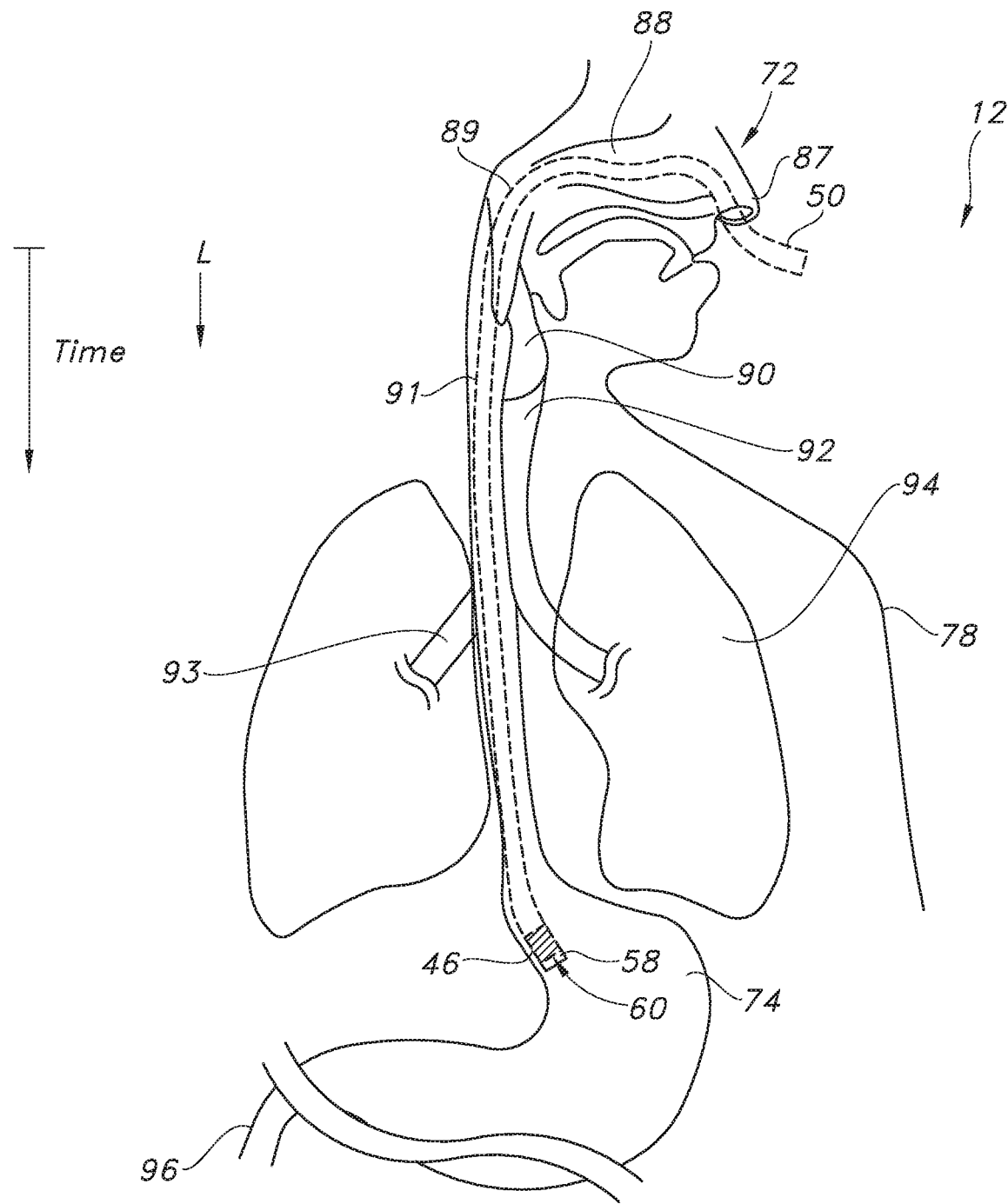
FIG. 7A is a top or plan view of a portion of the electronic catheter unit illustrating an enteral application involving insertion of a catheter into the stomach of a patient, where the anatomical location of the catheter within the body can be monitored via sound data captured by the acoustic sensor of the present invention.
Figure 7B:
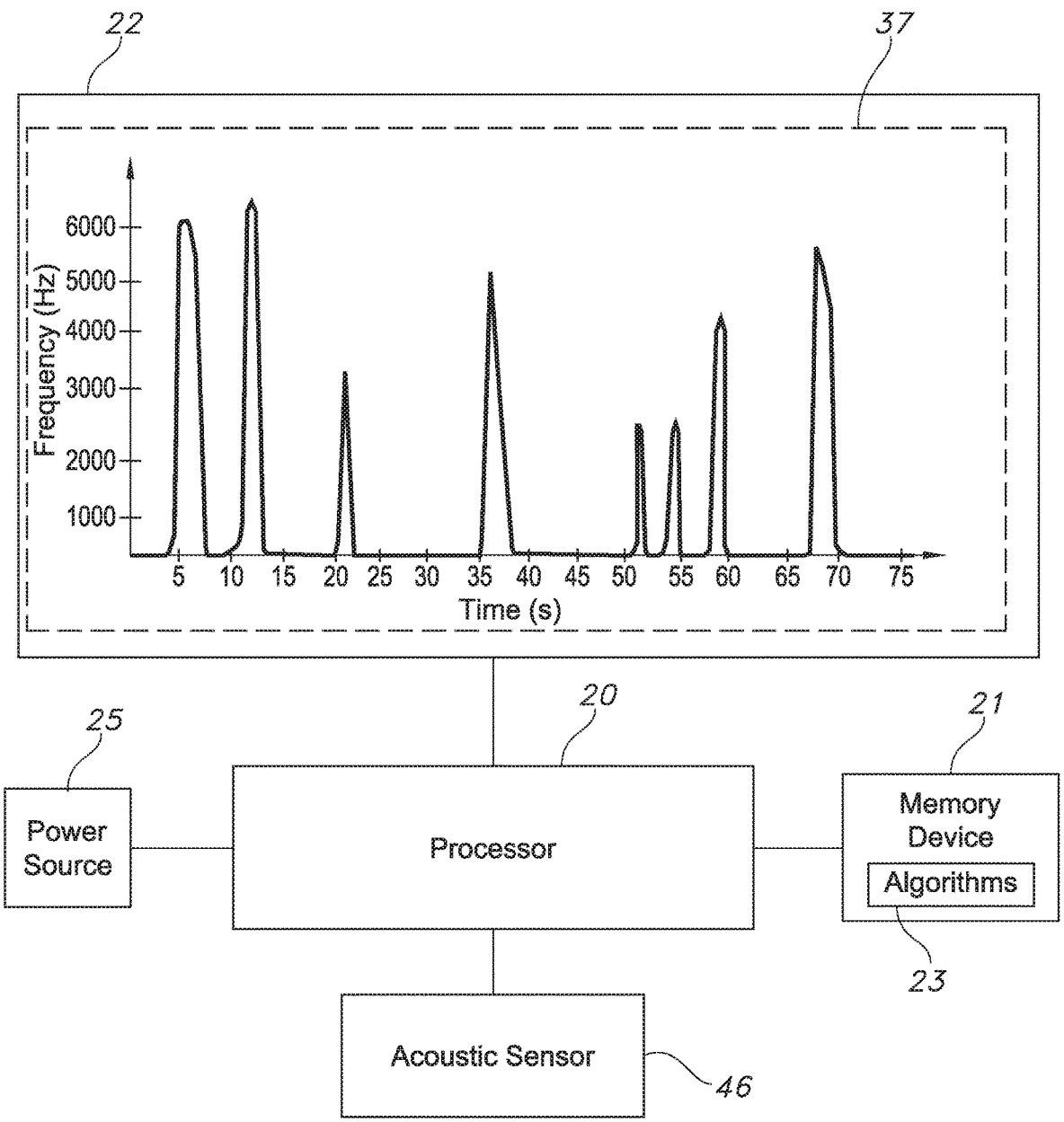
FIG. 7B is a schematic view of the catheter guidance system of the present invention as the system captures sound data associated with contact noises as the catheter of FIG. 7A comes into physical contact with the esophagus and other anatomical regions of the digestive tract in real-time via the acoustic sensor of the present invention.

Likewise, as shown in FIGS. 7A and 7B, when the distal end or tip 60 of the catheter 50 is inserted into the nostril 87 of the patient and is advanced through the nasal cavity 88, past the nasopharynx 89, and into the esophagus 91 just past the epiglottis 90, and then into the stomach 74, as the acoustic sensor 46 is continuously receiving, recording, and/or processing sound waves propagating through the opening 180 in the distal end 60 of the catheter 50 (whether the acoustic sensor 46 is in the lumen 70 of the catheter 50 itself or in a sampling chamber 54 as shown in FIGS. 1 and 4), the frequency versus time spectrogram graph 37 (FIG. 7B) displayed or otherwise communicated by the processor 20, such as via the display device 22, may show random spikes associated with contact noises as the distal end or tip 60 of the catheter 50 travels into the digestive tract and not into the respiratory system. With insertion of the catheter 50 accurately into the digestive tract, the random spikes associated with contact noise may continue as the distal end or tip 60 reaches the esophagus 91 and is not exposed to the rhythmical pattern of breathing associated with inspiration and expiration, where the frequency versus time spectrogram graph would show a repetitive pattern.

Figure 8A:
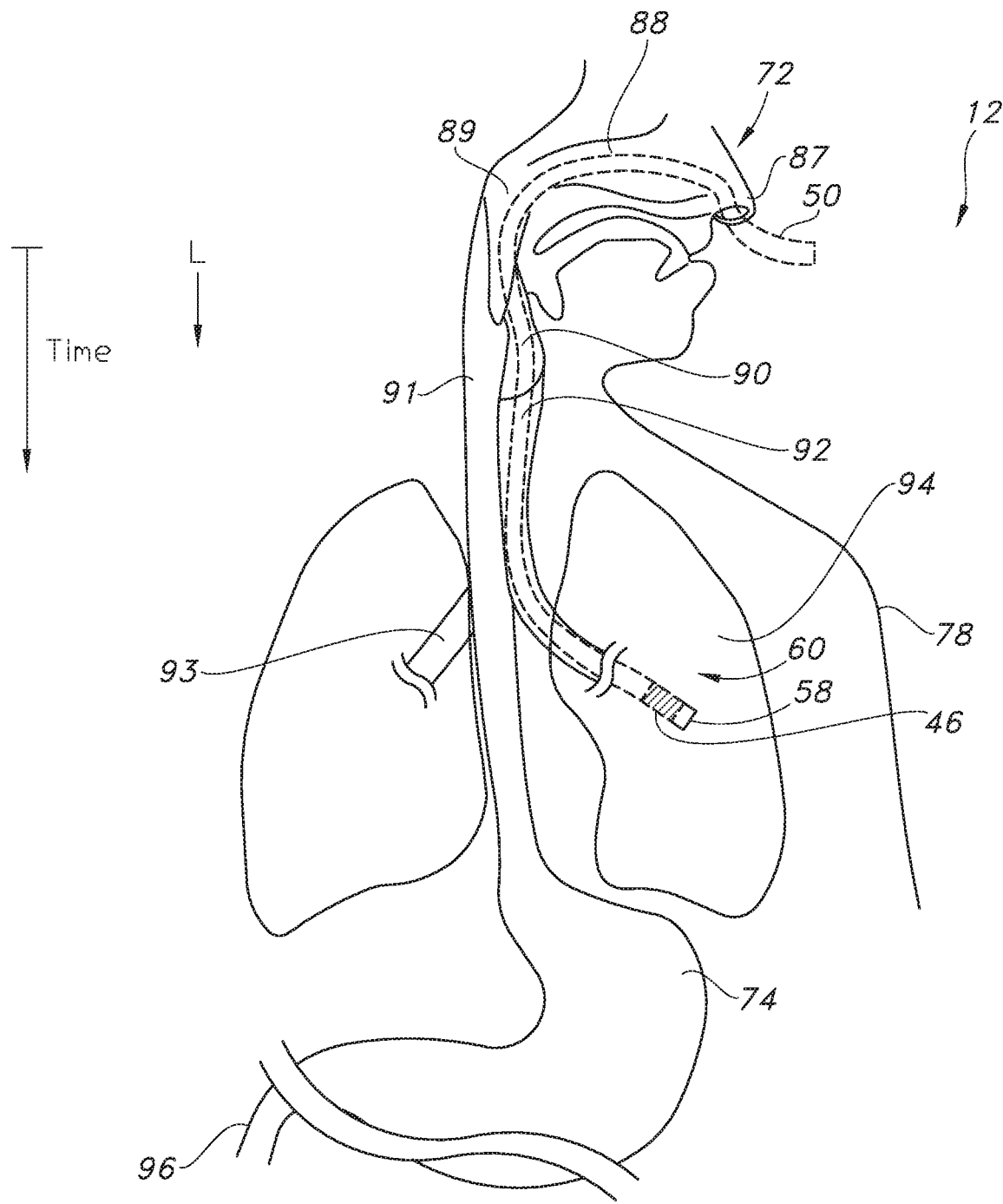
FIG. 8A is a top or plan view of a portion of the electronic catheter unit illustrating an enteral application involving insertion of a catheter erroneously into the lung of a patient, where the anatomical location of the catheter within the body can be monitored via sound data captured by the acoustic sensor of the present invention.
Figure 8B:
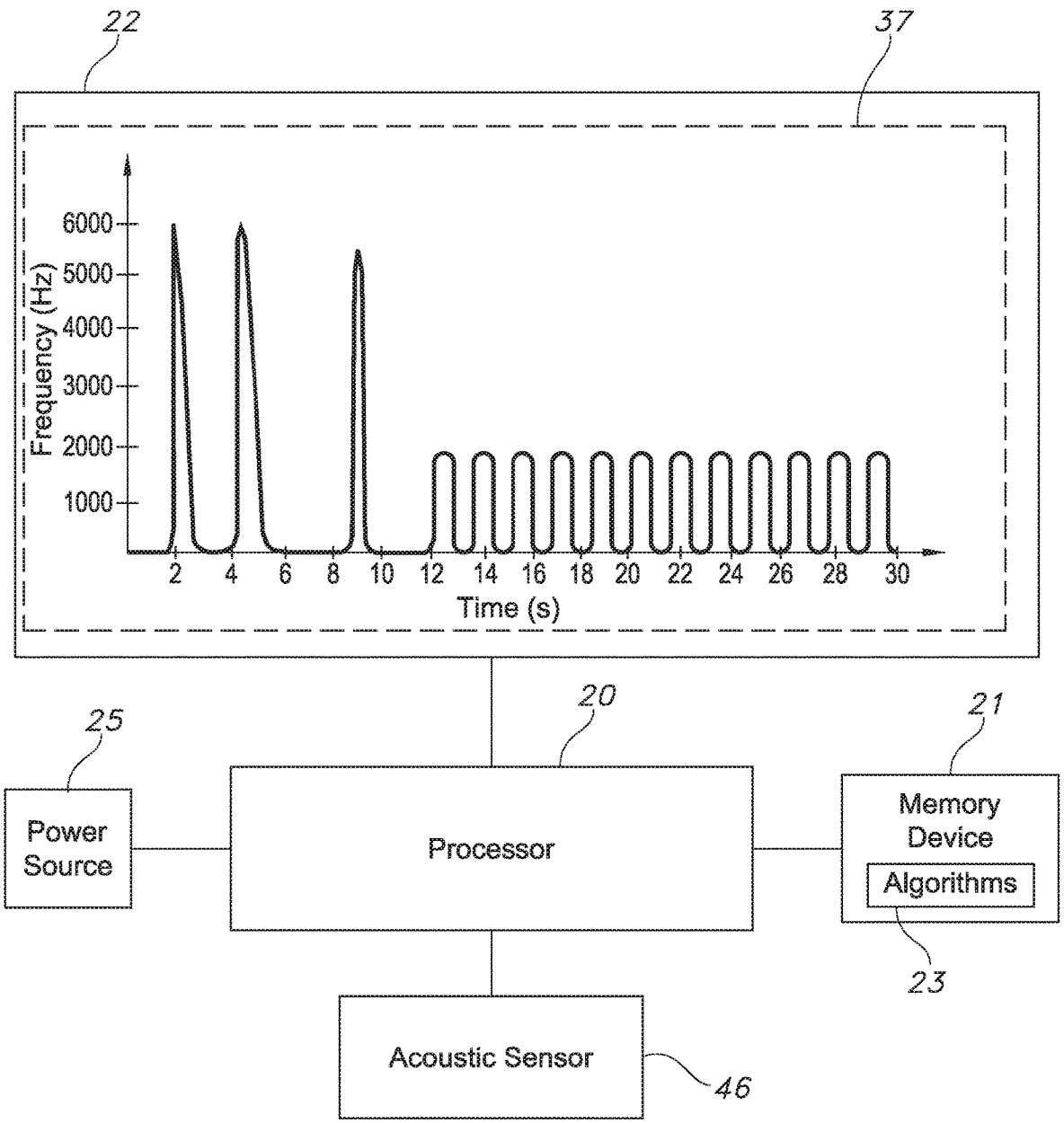
FIG. 8B is a schematic view of the catheter guidance system of the present invention as the system captures sound data associated with respiration sound waves (e.g., rhythmical sound waves) as air passes over an opening in the distal tip of the catheter of FIG. 8A in real-time via the acoustic sensor of the present invention.

On the other hand, as shown in FIGS. 8A and 8B, when the distal end or tip 60 of the catheter 50 is inserted into the nostril 87 of the patient and is advanced through the nasal cavity 88, past the nasopharynx 89, and into the trachea 92 just past the epiglottis 90, and then into the bronchi 93 or lungs 94, as the acoustic sensor 46 is continuously receiving, recording, and/or processing sound waves propagating through the opening 180 in the distal end 60 of the catheter 50 (whether the acoustic sensor 46 is in the lumen 70 of the catheter 50 itself or in a sampling chamber 54 as shown in FIGS. 1 and 4), the frequency versus time spectrogram graph 37 (FIG. 8B) displayed or otherwise communicated by the processor 20, such as via the display device 22, may show a repetitive, rhythmical pattern (e.g., a sinusoidal wave) as the distal end or tip 60 of the catheter 50 travels into the respiratory system. With insertion of the catheter 50 inaccurately into the respiratory system, the inaccurate placement will quickly become apparent to the health care provider within a matter of seconds of the insertion procedure (e.g., once the distal end or tip 60 reaches the trachea 92, the bronchi 93, or the lungs 94) as the distal end or tip 60 of the catheter will be exposed to air movement that tracks the rhythmical pattern of breathing associated with inspiration and expiration, where the associated sound waves recorded by the acoustic sensor 46, in turn, exhibit this rhythmical, repetitive pattern. At this point, the health care provider can be alerted to remove the tubing assembly 14 from the respiratory system and start a new procedure to accurately place the distal end or tip 60 of the catheter 50 into the digestive tract for enteral feeding.

Further, as an alternative or in addition to recording sound data via the acoustic sensor 46 over time and observing the sound data on a frequency versus time spectrogram graph 37 or other type of plot, the health care provider can also verify accurate placement of the catheter 50 in the esophagus 91 rather than the trachea 92 by observing for the presence or absence of a plurality of markings 112 uniformly spaced along the external surface of the catheter 50. As described above, such markings 112 can be used in conjunction with the acoustic sensor 46 to determine accurate placement of the catheter 50. These markings 112 can function as placement markers which assist the user in assessing the depth that the catheter 50 is placed within the body 78. For instance, when the acoustic sensor 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the health care provider can be alerted to start monitoring the graphs 37 on the display device 22 to observe the frequency versus time spectrograms plotted from sound data measured by the acoustic sensor 46 or to start monitoring for a visual indication, auditory indication, or both that the catheter 50 has be inserted into the correct (e.g., digestive tract) or incorrect location (e.g., respiratory tract). For example, if the appearance of a rhythmical pattern (e.g., a sinusoidal wave) on a frequency versus time spectrogram shown on the display device 22 is present once the markings 112 are no longer visible outside the body 78, then the user will be able to determine that the catheter 50 has been improperly inserted into the trachea 92 instead of the esophagus 91, and the catheter 50 should be immediately retracted.

Regardless of the particular method by which proper placement of the catheter 50 is determined, once the distal end or tip 60 of the catheter 50 has been accurately placed within the desired location in the digestive tract, the health care provider can then optionally remove the acoustic sensor 46, particularly when the acoustic sensor 46 is located within the lumen 70 of the catheter and includes a wired connection, where the wire assembly 62 electrically connects the acoustic sensor 46 to the processor 20 via the electrical connector or controller coupler 36, while the position of the catheter 50 is maintained. The health care provider can then attach medicine and nutritional delivery tubes to the y-port connector 44 for introducing fluids into the body (e.g., digestive tract) for medical treatment. On the other hand, if the acoustic sensor 46 is wireless or is placed within the sampling chamber 54, the acoustic sensor 46 can optionally be left in place, and the health care provider can then attach medicine and nutritional delivery tubes to the y-port connector 44 for introducing fluids into the body (e.g., digestive tract) for medical treatment.

Moreover, in conjunction with the acoustic sensor 46 described herein, the system 2 also contemplates the use of an optional signal generator 58 and associated transceiver 32 that can be used to track the position of the distal end 60 of the catheter 50 as it is being inserted into the patient's body 78. In one embodiment, the signal generator 58, which is located at the distal end 60 of the catheter and can be connected to the apparatus 10 via the controller coupler/electrical connected 36 and the wire assembly 62 (see FIGS. 1, 3, and 4), can be formed through a plurality of spirals or coils of wires. Further, the apparatus 10 can be configured to transmit electrical current through the wires such that the current travels in a circular path defined by the coils. This circular motion of current produces an electromagnetic field. In operation, when the apparatus 10 sends electrical current to the coils of the signal generator 58, the coils then transmit a signal or electromagnetic field capable of being detected by the non-invasive transceiver 32. The transceiver 32 then detects the electromagnetic field or signal generated by the signal generator 58 inside the patient's body 78 and the system 2 analyzes the resulting information to cause the display device 22 and the printer 28 to produce additional graphics 37 which can assist the health care provider in a catheter placement procedure in conjunction with sound data acquired by the acoustic sensor 46. For instance, the system 2 can include a memory device 21 including machine readable instructions and one or more computer programs (which, for example, may include a plurality of algorithms 23) which are used by the processor 20 to process the signal data produced by the signal generator and transmitted by the transceiver 32, after which the processed data is displayed in graphical format on the display device 22 corresponding to the location of the distal end 60 of the catheter 50 within the patient's body 78. In one particular embodiment, the transceiver 32 can be used to determine the distance the signal generator 58 is from the transceiver 32 and its dept in the patient's body 78 can communicate with the display device 22 via the processor 20 to show a reference image of a non-subject body and an image of the signal generator 58 located on the display device 22 with the reference image.

It should also be appreciated that the tubing assembly, electronic catheter unit and catheter position guidance system of the present invention can be used in a variety of catheter procedures and applications. These procedures may involve the treatment of the digestive or gastrointestinal tract or other portions of the human body. These procedures may involve treatment of humans by physicians, physician assistants, nurses or other health care providers. In addition, these procedures may involve treatment of other mammals and animals by veterinarians, researchers and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A catheter guidance system comprising:
   (a) a processor;
   (b) a power source;
   (c) a display device; and
   (d) a tubing assembly comprising:
      a catheter having a proximal end and a distal end and extending in a longitudinal direction, wherein the proximal end and the distal end define a lumen therebetween; and
      an acoustic sensor, wherein the acoustic sensor is located upstream from the distal end of the catheter, wherein the acoustic sensor is protected from fluid ingress by a flexible coating surrounding the acoustic sensor;
   wherein the acoustic sensor communicates sound data acquired directly by the acoustic sensor from sound waves traveling through the lumen from an opening in the distal end of the catheter to the processor in real-time via an electrical connection;
   wherein the display device is coupled to the processor and displays a graph of the sound data communicated by the acoustic sensor;
   wherein the catheter guidance system alerts a user as to correct placement of the catheter in a digestive tract of a patient or alerts the user as to incorrect placement of the catheter in a respiratory tract of the patient, wherein the incorrect placement is determined by the presence of sinusoidal respiratory patterns associated with the sound data acquired directly by the acoustic sensor.

2. The catheter guidance system of claim 1, further comprising a memory device storing instructions which, when executed by the processor, cause the processor to (i) interpret the sound data communicated by the acoustic sensor and (ii) cause the catheter guidance system to alert the user as to correct placement of the catheter in the digestive tract of the patient or alert the user as to incorrect placement of the catheter in the respiratory tract of the patient based on the interpretation of the sound data.

3. The catheter guidance system of claim 1, wherein the acoustic sensor is located within the lumen of the catheter or within a sampling chamber.

4. The catheter guidance system of claim 1, wherein the acoustic sensor is contained within a microelectro-mechanical system (MEMS) microphone.

5. A method for determining if a catheter is placed within a digestive tract of a body of a patient, the method comprising:
   (a) inserting a distal end of a tubing assembly into an orifice of the body, wherein the tubing assembly comprises:
      the catheter, wherein the catheter has a proximal end and a distal end and extends in a longitudinal direction, wherein the proximal end and the distal end define a lumen therebetween; and
      an acoustic sensor, wherein the acoustic sensor is located upstream from the distal end of the catheter, wherein the acoustic sensor is contained within a microelectro-mechanical system (MEMS) microphone, and wherein the acoustic sensor is protected from fluid ingress by a flexible coating surrounding the acoustic sensor;

(b) electrically connecting the acoustic sensor to a processor via a wired connection or a wireless connection;

(c) activating the acoustic sensor, wherein the acoustic sensor acquires sound data from sound waves traveling through the lumen from an opening in the distal end of the catheter and communicates the sound data to the processor in real-time via the wired connection or the wireless connection;

(d) advancing the distal end of the catheter inside the body in a direction away from the orifice while the acoustic sensor is activated; and (e) observing a graph of the sound data on a display device coupled to the processor, wherein the display device alerts a user as to correct placement of the catheter in the digestive tract of the patient or alerts the user as to incorrect placement of the catheter in a respiratory tract of the patient, wherein the incorrect placement is determined by the presence of sinusoidal respiratory patterns associated with the sound data acquired directly by the acoustic sensor.

6. The method of claim 5, wherein a memory device stores instructions which, when executed by the processor, cause the processor to (i) interpret the sound data communicated by the acoustic sensor and (ii) cause the display device to communicate whether or not the catheter is placed within the digestive tract of the patient based on the interpretation of the sound data.

7. The method of claim 5, wherein the orifice is a nose or a mouth.

8. The method of claim 5, wherein the acoustic sensor is located within the lumen of the catheter or within a sampling chamber.

9. The method of claim 5, wherein the acoustic sensor is contained within a microelectro-mechanical system (MEMS) microphone.

* * * * *